United States Patent [19]

Lundström

[11] Patent Number: 5,222,906

[45] Date of Patent: Jun. 29, 1993

[54] EXHAUSTING DEVICE

[75] Inventor: Barry Lundström, Skellefteå, Sweden

[73] Assignee: Fumex AB, Skellefteå, Sweden

[21] Appl. No.: 721,472

[22] PCT Filed: Jan. 3, 1990

[86] PCT No.: PCT/SE90/00004

§ 371 Date: Sep. 4, 1991

§ 102(e) Date: Sep. 4, 1991

[87] PCT Pub. No.: WO90/07991

PCT Pub. Date: Jul. 26, 1990

[30] Foreign Application Priority Data

Jan. 12, 1989 [SE] Sweden .............................. 8900105

[51] Int. Cl.⁵ ............................................... F23J 11/04
[52] U.S. Cl. ...................................................... 454/64
[58] Field of Search ...................... 104/52; 454/63, 64,
454/65; 126/294 D; 285/302

[56] References Cited

U.S. PATENT DOCUMENTS

| | | | |
|---|---|---|---|
| 495,141 | 4/1893 | Norton | 126/294 D X |
| 1,691,816 | 11/1928 | Klyce | 285/302 X |
| 2,023,263 | 12/1935 | Blume | 454/63 X |
| 2,415,740 | 2/1947 | Gammack | 285/302 X |
| 2,665,647 | 1/1954 | Knutson et al. | 104/52 |
| 3,435,752 | 4/1969 | Capstran | 454/64 |
| 4,086,847 | 5/1978 | Overmyer | 454/64 |

FOREIGN PATENT DOCUMENTS 1506886  4/1978  United Kingdom ................. 454/65

Primary Examiner—Harold Joyce
Attorney, Agent, or Firm—Cushman, Darby & Cushman

[57] ABSTRACT

A suction device for the removal by suction of waste gases or other environmentally harmful gases from a working location, e.g., from the exhaust pipe of an automotive vehicle, including a suction line which is connected to a central suction means or to a suction fan and one end of which is intended to be connected temporarily to, e.g., an exhaust pipe of an automotive vehicle or the like for the purpose of removing by suction exhaust gases deriving from the engine of the vehicle. In order to enable the suction line of such suction devices to be extended manually, even when the suction line is suspended vertically directly from a ceiling-mounted main suction line, the suction line is telescopic and a spring is mounted between the telescoping part of the suction line, such that the spring will be tensioned when the suction line is extended and therewith assist in restoring the suction line to its retracted state.

15 Claims, 2 Drawing Sheets

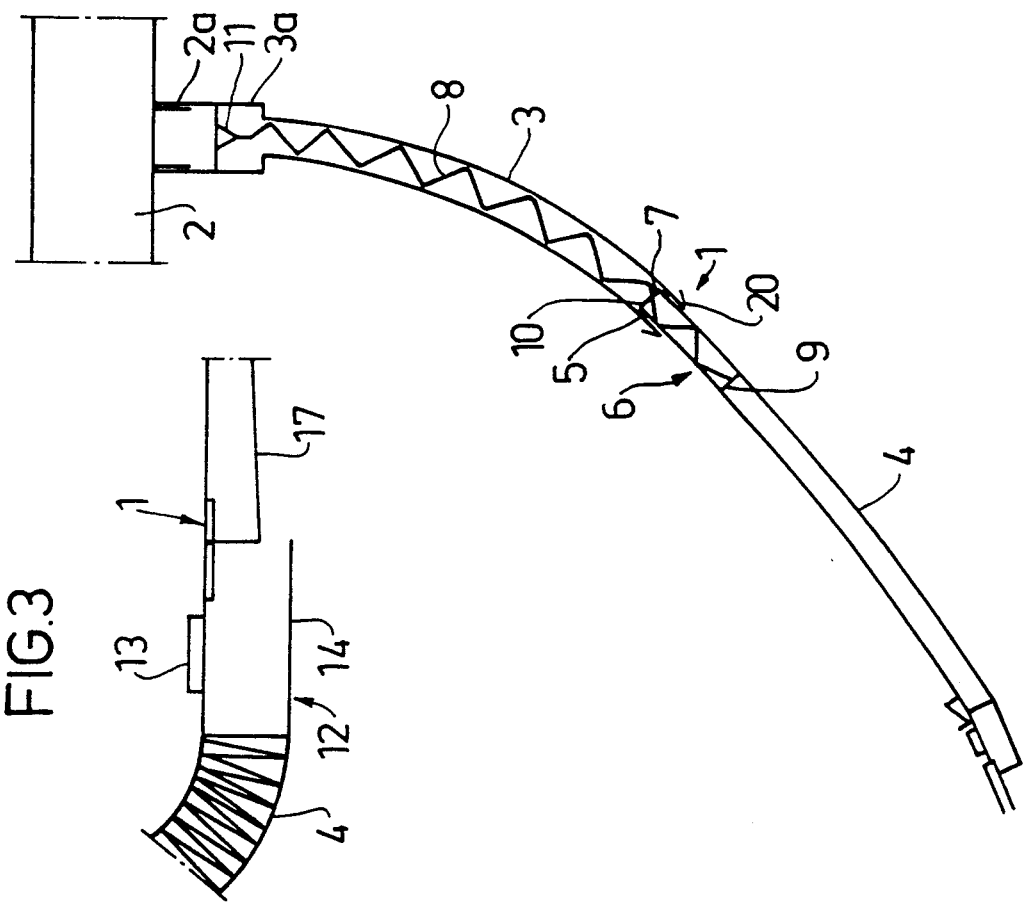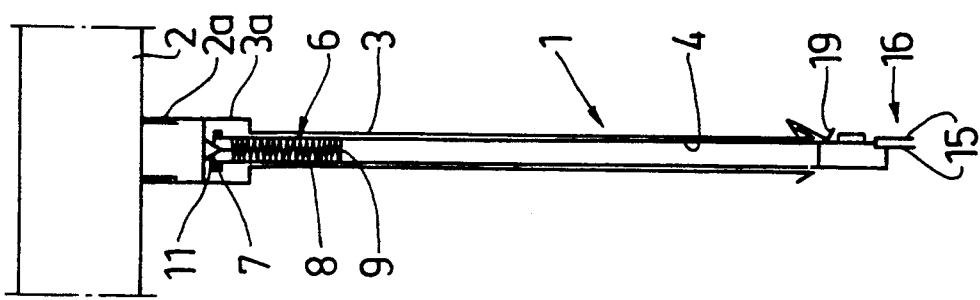

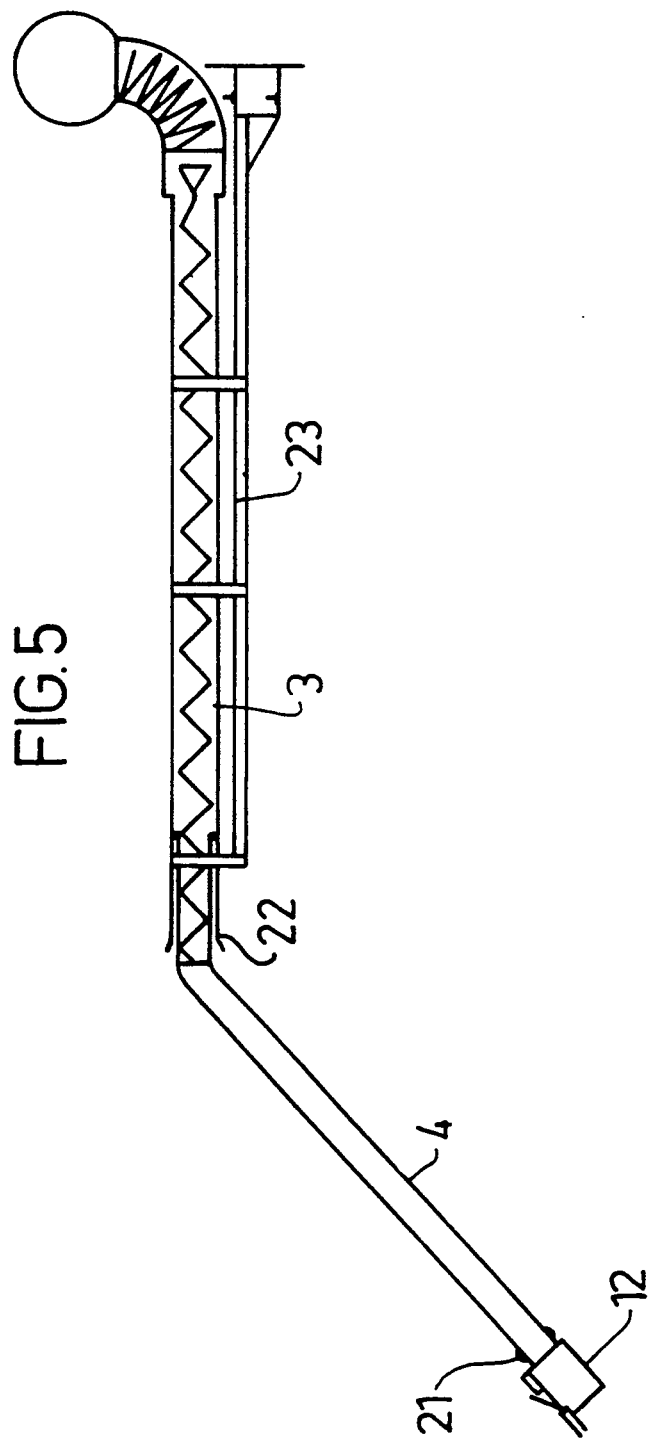

EXHAUSTING DEVICE

BACKGROUND OF THE INVENTION

The present invention relates to an exhaustion device of the kind which is intended for the removal by suction of exhaust gases and other environmentally harmful gases from a working area or location, or from the exhaust pipe of an automotive vehicle, and which comprises a suction line which is connected at one end thereof to a central suction means or to a suction fan and the other end of which is intended to be connected temporarily to the working location or to the exhaust pipe of an automotive vehicle, or some like location, for the purpose of removing therefrom by suction waste or exhaust gases generated in the working location or by the automotive vehicle.

Exhaustion devices of this kind are used in vehicle workshops, vehicle-inspection localities and vehicle-repair shops which are intended for other types of motor vehicle than cars, lorries (trucks) and buses, e.g. for such vehicles as tractors, forestry machines and agricultural machines. The exhaustion devices are operative to remove the exhaust gases generated when running tests on the engines of such vehicles and/or when bench-testing the engines in closed areas. Such exhaustion devices are also used in other kinds of workshops and also in laboratories, for the purpose of removing by suction environmentally harmful gases and vapours that are generated in such working locations, e.g. for the removal of welding gases from welding sites and from cutting machines. Exhaustion devices of this kind normally include a flexible suction hose which is provided at one end thereof with a connector or like device operative to connect the hose to the exhaust pipe of an automotive vehicle, or to a gas-collecting box or like device arranged over a workplace. In order to enable the hose carrying the connector to be connected, for instance, to the exhaust pipe of a vehicle, it is necessary for the hose to have a given length, and the greater the length of hose available, the greater the spatial working range of the exhaustion device. In those periods when the device is not being used to remove exhaust gases or other environmentally harmful gases or vapours, it is necessary for the hose to be stowed in some way or another, so that the hose will not be left hanging, with part of the hose lying on the floor, and therewith cause an obstacle to other work.

In order to overcome this drawback, it is known to wind the hose onto a reel fixed to the ceiling or a wall of the locality concerned, such as to enable a required length of hose to be uncoiled from the reel and the hose connected to the vehicle exhaust pipe. Such reels are normally provided with a spring device which is operative to recoil the hose automatically, i.e. with a powerful spring which when the hose is pulled from the reel is tensioned to an extent sufficient to rotate the reel automatically when the pulling force is removed, and thus re-wind the hose. In order to achieve automatic re-coiling of the hose after use in the case of an exhaustion device of such a kind, it is necessary, however, to use an extremely powerful spring with the subsequent drawback that an extremely large force must be applied to the hose in order to draw the hose from the reel, particularly when the hose is to be uncoiled to the extent of its full length. If the hose is not unwound to its full length, since a shorter hose-length will suffice, as is often the case, the flow resistance through the remaining turns of the hose will increase, resulting in a reduction in the exhausting ability of the device.

As a result of these and other drawbacks this kind of gas-exhausting device has been used to an increasingly smaller extent and the device has been replaced with exhaustion devices with which a required length of hose can be withdrawn from within a tube which is carried substantially horizontally by a wall-mounted, pivotal carrier arm and which is connected to a suction fan or to a central suction outlet located in a main suction line. The end of the hose located in the tube is sealed against the tube such that when the hose is release and the connector is closed and the suction-effect activated, the hose will be subjected to a subpressure which is operative to withdraw the length of hose extended from the tube to a predetermined position within the tube, in which position the hose length is withdrawn and will not therefore present an obstacle to other working activities. The subpressure required to withdraw the hose into the tube is achieved by providing the connector mounted on the hose with a cap or valve means operative to close the connector at the instance of disengaging the connector from an exhaust pipe, therewith enabling the subpressure required to retract the length of hose to be obtained.

The majority of known exhaustion devices are provided with such caps or valve means, primarily for the purpose of preventing air from being sucked from the locality concerned when the device is not in use, and therewith to prevent the occurrence of draughts and heat losses. Such caps are also operative to hold the hose connector in firm abutment with the outer surface of the vehicle-exhaust pipe, such as to ensure that the connector is not unintentionally disengaged from the exhaust pipe when removing exhaust gases therefrom by suction.

It is also known with this type of exhaustion device to use a wall-mounted or column-mounted winch, for the purpose of extending the substantially horizontally carried suction hose from its tube and for retracting the hose into the tube subsequent to use. In this case, the winch line is attached to the inner end of the suction hose and must therefore extend through the tube surrounding said hose, causing troublesome sealing problems as a result thereof. Consequently, with this type of exhaustion device, there is a serious risk that air will be sucked from the locality concerned, even when the device is not in use.

All of these known exhaustion devices equipped with retractable suction hoses which are partially carried substantially horizontally have the disadvantage of requiring the presence of a wall or support column in order to be mounted in the locality concerned, and consequently it is not possible to connect this type of exhaustion device to a ceiling-suspended main suction line which is located at a position remote from both walls and support columns. It is true that suction devices provided with ceiling mountable hose-reels can be used, although this solution is very expensive in comparison with the use of a suction hose which hangs directly from the main suction line and which is a very simple and inexpensive alternative from the aspect of cost, and although problems are experienced with regard to retracting the hose when not in use. This problem can be overcome with the aid of a ceiling-mounted balancing block of the kind described, for instance, in Swedish Published Specification 7709129-6 (publication No. 417162) or with a hose winch which is operative to coil the hose so that the hose will not constitute an obstruction when not in use. In the case of suction-hose suspension arrangements of this kind, the suction hose will present a bend, even when connected to a vehicle-exhaust pipe, resulting in increased flow resistance, and consequently such suction-hose suspension-devices have not been used to any great extent in practice.

SUMMARY OF THE INVENTION

Accordingly, the object of the present invention is to provide a gas-exhaustion device of the kind defined in the introduction which is not emcumbered with the drawbacks of known gas-exhaustion devices and which is so constructed that the suction hose can be extended in a ready and simple fashion and connected, for instance, to the exhaust pipe of an automotive vehicle without the occurence of flow-preventing bends in the hose, and can be restored to its original starting position or to a retracted position readily and easily, even when mounted vertically directly to a ceiling-suspended main suction line, and also to provide such an exhaustion device which while of simple construction is nevertheless reliable in operation.

This object is achieved with a gas-exhaustion device constructed in accordance with the present invention. According to one preferred embodiment of the exhaustion device, the suction line of device is telescopic and has a preferably helical spring mounted between the telescopic sections of the suction line, such that the spring will be tensioned when extending the telescopic suction-line and therewith assist in returning the suction line to its withdrawn or retracted position. The telescopic suction line preferably comprises a fixedly mounted outer part and an inner part which is moveable in relation to the outer part, with the spring being positioned between the outer and inner suction-line parts. In the case of this embodiment, the outer suction-line part may have the form of a rigid tube, as may also the inner suction-line part, although it is preferred that both the outer part and the inner part have the form of a flexible, reinforced hose.

In the case of one very advantageous embodiment of the inventive exhaustion device, the inner part of the suction line is configured at one end thereof with a seating for a conical valve provided in the outer part of the suction line. This conical valve co-acts with the seating when the suction line is retracted, such as to prevent air from being sucked from the locality concerned when the exhaustion device is not in use. The spring incorporated in the present device is pretensioned to some extent, so that the spring will assist in holding the conical valve pressed against the valve-seating of the inner suction-line part when the suction line occupies its withdrawn or retracted position. This valve arrangement also enables the nozzle by means of which the suction line of the suction device is connected to the exhaust pipe of a motor vehicle to be simplified and obviates the need for the cap or valve-means required by the above-described known devices.

BRIEF DESCRIPTION OF THE DRAWINGS

The invention will be described in more detail with reference to the accompanying drawings, in which, FIGS. 1 and 2 are schematic, sectional side views of one embodiment of the inventive exhaustion device constructed for vertical suspension of the suction line in a retracted and extended position respectively;

FIG. 3 shows in larger scale one embodiment of a connector for connecting the suction line to the exhaust pipe of a motor vehicle; and FIGS. 4 and 5 illustrate schematically and in section a wall-mounted or column-mounted embodiment of an inventive exhaustion device, and show the suction line in its retracted and extended positions respectively.

DETAILED DESCRIPTION

The exhaustion device comprises a telescopic suction line 1 which is connected, in a known manner, to a main suction line 2 or to a suction fan which is common to one or more such exhaustion devices. The illustrated suction line comprises two parts, namely an outer part 3 which has at one end thereof a flexible hose part 3a or tube part of larger diameter than the outer part 3 and which is connected by the part to the main suction line 2, the main suction line being conveniently provided with a connection stub-pipe 2a, and is thus firmly connected to the main suction line 2, and an inner part 4 which is positioned within the outer part 3 and which is moveable relative to the outer part. The outer diameter of the inner part 4 will preferably not deviate to any large extent from the inner diameter of the outer part, and for the purpose of avoiding air being, sucked in between the outer and inner parts 3, 4 of the suction line, a rubber sleeve 5 or some like sealing device is preferably fitted to the internal, surface of the free end of the outer part of the line, said sleeve 5 also functioning as a slide shoe for facilitating movement of the inner part relative to the outer part 3 when extending and retracting the suction line. In this case, the free end of the outer part of the suction line may be collared, as shown particularly in FIGS. 3 and 4.

One end of a spring 8, preferably a helical spring, is attached to the inner end-part 6 of the inner part 4 of the suction line with the aid of a pin 9 secured in the inner part 4. The spring 8 is preferably attached at a distance from the inner end 7 of the end-part 6 the other end of the spring is attached to the inner end of the outer suction-line part 3 or to the main suction line 2, or to some other suitable part. When the inner suction-line part 4 is extended from the position illustrated in FIG. 1, the spring 8 will be tensioned and therewith function as a return spring to facilitate retraction of the inner part 4 into the outer part 3 of the suction line. The spring force exerted by the spring 8 is progressive and is adapted to the weight of the inner suction-line part, so as to be able to retract the inner part 4 from a fully extended position, even when the inner part extends vertically as illustrated in FIGS. 2 and 3.

The inner end 7 of the inner suction-line part of the exhaustion device is configured to form a valve seat 10 which when the inner part is fully retracted or withdrawn co-acts with a conical valve means 11 fixedly mounted in the outer part 3 of the suction line or in the main suction line 2. Thus, when the inner part 4 of the suction line is in its fully retracted position, the valve means will effectively prevent air from being sucked from the room or locality concerned, through the suction line 1. The spring 8 is preferably pre-tensioned so that when the inner part of the suction line is in its fully retracted position, as illustrated in FIG. 1, the spring will exert a given force and hold the seat 10 on the inner suction-line part in abutment with the valve means 11. In the case of embodiments which include the valve means 11, the spring 8 when in its compressed state will preferably be capable of being accommodated within the end-part 6 of the inner suction-line part, as illustrated, for instance, in FIG. 1. Immediately when the inner part 4 is extended, the valve seat 10 of said inner part will move away from the valve means 11 and therewith automatically open the suction-connection to the suction source.

This valve arrangement enables the connecting devices 12 required for connecting the present type of exhaustion device to, for instance, a vehicle-exhaust pipe, to be greatly simplified, and one such simplified connector 12 is illustrated in FIG. 3. The illustrated connector 12 comprises a metal casing 14, preferably a cylindrical casing which is provided with a handle or handgrip 13 and connected to the inner suction-line part 4. The connector also comprises a gripping fork 16 having two legs 15 and is intended to be fitted to the exhaust pipe 17 concerned. The fork-legs may be provided with friction-enhancing material, such as rubber, on at least their mutually opposing side surfaces, so as to improve the grip exerted by the legs. When the inner suction-line part is extended, the spring 8 will act with an obliquely and outwardly directed suction-line restoring force, and consequently the spring will have a jamming effect on the gripping fork 16 in positive retention of the connector 12 of the exhaustion device to the vehicle-exhaust pipe 17.

FIGS. 4 and 5 illustrate a connector 12 which is provided with a gripping fork 16. One leg 15 of the gripping fork can be swung outwardly against the action of a spring (not shown) by means of a hand grip 18, to facilitate fitting of the connector to a vehicle-exhaust pipe. The leg is operative to hold the connector 12 firmly clamped to the exhaust pipe, as a result of the spring load acting on the leg.

For the purpose of holding the inner suction-line part 4 in a fully retracted position in the outer suction-line part 3, the connector 12 may be provided with a spring-loaded hook 19 which co-acts with a locking lip or flange 20, preferably a circumferential flange, provided on the free end of said outer part 3. This retention of the inner part 4 in the outer part 3 can also be achieved with the aid of a snap-fastener comprising an external bead 21 or the like on the inner part 4 and an internal bead 22 or the like on the end part of the outer suction-line part, the beads co-acting mutually in a known manner.

FIGS. 4 and 5 illustrate an embodiment of the present invention in which the outer part 3 of the suction line is carried by an arm 23 pivotally mounted on a wall or column. The suction line 1 is connected to a main suction line 2 in the aforedescribed manner, and the part 3a will preferably include a hose part, particularly in those cases when the carrier arm 23 is pivotally mounted.

Although both the inner part 4 and the outer part 3 of the suction line 1 may be rigid tubular members, it is preferred that the outer part 3 have the form of a rigid tube and the inner part 4 the form of a flexible hose. In those instances when the inner part of the suction line also includes in a sheet-metal tube, e.g. a helical tube of limited flexibility, the outer part 3 of the suction line will preferably be adjustable to different angular positions in relation to the floor of the location concerned. Particularly in the case of embodiments in which the suction line is suspended vertically, both the outer part 3 and the inner part 4 of the suction line will preferably have the form of a flexible, reinforced hose, preferably a helical-wound reinforced hose.

The present invention is not restricted to the aforedescribed and illustrated embodiments, and modifications and changes can be made within the scope of the inventive concept defined in the following claims.

I claim:

1. An exhaustion device for directing the flow of gases output from a source to a suction device inlet, comprising:
   a first hollow tubular member of first predetermined diameter having an inlet end and an outlet end, said first hollow tubular member coupled at the outlet end thereof to the suction device inlet;
   a second hollow tubular member of second predetermined diameter, smaller than said first predetermined diameter having an inlet end and an outlet end, said second hollow tubular member telescopically extendable from an inlet end of said first hollow tubular member; and
   a tension spring coupled at one end to the outlet end of said first hollow tubular member and at the other end to said second hollow tubular member means coupling the inlet end of said second hollow tubular member to said source,
   wherein in a fully retracted position of said second hollow tubular member, said outlet end thereof sits firmly within said first hollow tubular member, said tension spring maintaining a constant pre-tension force on the second hollow tubular member, and
   wherein in a non-fully retracted position of said second hollow tubular member, said second hollow tubular member is tensioned by the retraction spring force exerted by the tension spring to facilitate retraction of the second hollow tubular member when it becomes disconnected from the source.

2. The exhaustion device of claim 1, wherein said tension spring is a coil spring.

3. The exhaustion device of claim 2, wherein said exhaustion device further comprises suction shut-off means to matingly couple said first and second hollow tubular member, in the fully retracted position of the second hollow tubular member, to disengage suction action.

4. The exhaustion device of claim 3, wherein said suction shut-off means includes an annular valve seat provided on said outlet end of said hollow tubular member and a conical element provide on said outlet end of said first hollow tubular member.

5. The exhaustion device of claim 3, wherein said first hollow tubular member is a rigid tube.

6. The exhaustion device of claim 4, wherein said first hollow tubular member is a rigid tube.

7. The exhaustion device of claim 5, wherein said second hollow tubular member is a flexible tube.

8. The exhaustion device of claim 5, wherein said second hollow tubular member is a rigid tube.

9. The exhaustion device of claim 3, wherein both said first and second hollow tubular members are flexible hoses.

10. The exhaustion device of claim 4, wherein both said first and second hollow tubular members are flexible hoses.

11. The exhaustion device of claim 1, further comprising an annularly slidable seal to facilitate telescopic operation of the second hollow tubular member within said first hollow tubular member, said annularly slidable seal being effectively provided therebetween.

12. The exhaustion device of claim 1, wherein said inlet end of said second hollow tubular member includes a gripping fork for secure attachment thereof to said source.

13. The exhaustion device of claim 12, wherein said source is an outlet of an automobile engine exhaust pipe.

14. The exhaustion device of claim 1, wherein said first hollow tubular member includes an angularly articulable joint therein, disposed between said outlet end thereof and said outlet end of said second hollow tubular member when said second hollow tubular member is in the fully retracted position.

15. The exhaustion device of claim 1, wherein:
said first and second hollow tubular members have longitudinal bores, and said tension spring extends within said longitudinal bores.

* * * * *